United States Patent [19]

Roth

[11] Patent Number: 5,273,995

[45] Date of Patent: Dec. 28, 1993

[54] [R-(R*R*)]-2-(4-FLUOROPHENYL)-β,δ-DIHYDROXY-5-(1-METHYLETHYL-3-PHENYL-4-[(PHENYLAMINO) CARBONYL]-1H-PYRROLE-1-HEPTANOIC ACID, ITS LACTONE FORM AND SALTS THEREOF

[75] Inventor: Bruce D. Roth, Ann Arbor, Mich.

[73] Assignee: Warner-Lambert Company, Morris Plains, N.J.

[21] Appl. No.: 660,976

[22] Filed: Feb. 26, 1991

Related U.S. Application Data

[63] Continuation of Ser. No. 384,187, Jul. 21, 1989, abandoned.

[51] Int. Cl.$^5$ ................... A61K 31/40; C07D 405/06
[52] U.S. Cl. .................... 514/422; 514/423; 548/517; 548/537
[58] Field of Search ............... 514/422, 423; 548/517, 548/537

[56] References Cited

U.S. PATENT DOCUMENTS

4,681,893  7/1987  Roth ........................... 514/223

OTHER PUBLICATIONS

J. Med. Chem. 1985, 28, 347–358—G. E. Stokker, et al. "3-Hydroxy-3-Methylglutaryl-Coenzyme a Reductase . . . ".
Tetrahedron Letters, vol. 28, No. 13, pp. 1385–1388, 1987 "Synthesis of an HMG–COA Reductase Inhibitor, . . . ".

*Primary Examiner*—Mary C. Lee
*Assistant Examiner*—Jacqueline Haley
*Attorney, Agent, or Firm*—Ronald A. Daignault

[57] ABSTRACT

[R-(R*,R*)]-2-(4-fluorophenyl)-β,δ-dihydroxy-5-((1-methylethyl)-3-phenyl-4-[(phenylamino)-carbonyl]-1H-pyrrole-1-heptanoic acid or (2R-trans)-5-(4-fluorophenyl)-2-(1-methylethyl-N,4-diphenyl-1-[2-(tetrahydro-4-hydroxy-6-oxo-2H-pyran-2-yl)ethyl]-1H-pyrrole-3-carboxamide; and pharmaceutically acceptable salts thereof.

12 Claims, No Drawings

[R-(R*R*)]-2-(4-FLUOROPHENYL)-β,δ-DIHYDROXY-5-(1-METHYLETHYL-3-PHENYL-4-[(PHENYLAMINO) CARBONYL]-1H-PYRROLE-1-HEPTANOIC ACID, ITS LACTONE FORM AND SALTS THEREOF

This is a continuation of U.S. application Ser. No. 07/384,187 filed Jul. 21, 1989, abandoned.

BACKGROUND OF THE INVENTION

Trans-(±)-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamides are among compounds of U.S. Pat. No. 4,681,893 having usefulness as inhibitors of cholesterol biosynthesis. The compounds therein broadly include 4-hydroxypyran-2-ones and the corresponding ring-opened acids derived therefrom.

It is now unexpectedly found that the enantiomer having the R form of the ring-opened acid of trans-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamide; that is [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid, provides surprising inhibition of the biosynthesis of cholesterol.

It is known that 3-hydroxy-3-methylglutaryl coenzyme A (HMG-CoA) exists as the 3R-stereoisomer. Additionally, as shown in the study of a series of 5-substituted 3,5-dihydroxypentanoic acids by Stokker et al., in "3-Hydroxy-3-methylglutaryl-Coenzyme A Reductase Inhibitors. 1. Structural Modification of 5-Substituted 3,5-Dihydroxypentanoic acids and Their Lactone Derivatives," *J. Med. Chem.* 1985, 28, 347-358, essentially all of the biological activity resided in the trans diastereomer of (E)-6-[2-(2,4-dichlorophenyl)ethenyl]-3,4,5,6-tetrahydro-4-hydroxy-2H-pyranone having a positive rotation. Further, the absolute configuration for the β-hydroxy-δ-lactone moiety common to mevinolin of the formula (1a)

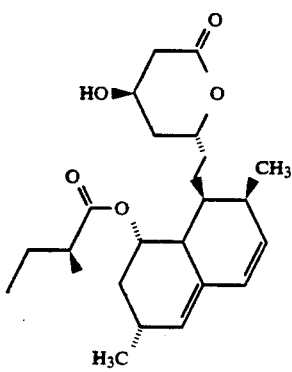

and compactin of the formula (1b)

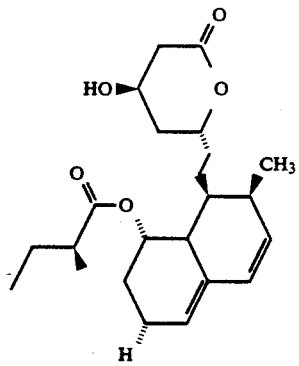

apparently is required for inhibition of HMG-CoA reductase. This is reported by Lynch et al. in "Synthesis of an HMB-CoA Reductase Inhibitor; A diastereoselective Aldol Approach in Tetrahedron Letters, Vol. 28, No. 13, pp. 1385-1388 (1987) as the 4R, 6R configuration.

However, an ordinarily skilled artisan may not predict the unexpected and surprising inhibition of cholesterol biosynthesis of the present invention in view of these disclosures.

SUMMARY OF THE INVENTION

Accordingly the present invention provides for compounds consisting of [R-(R*,R*)]-2-(4-fluorophenyl)-β,δ-dihydroxy-5-((1-methylethyl)-3-phenyl-4-[(phenylamino) carbonyl]-1H-pyrrole-1-heptanoic acid (compound of formula I), pharmaceutically acceptable salts thereof and (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide (the lactone form of the heptanoic acid or compound of formula II).

The present invention also relates to a pharmaceutical composition, useful as a hypocholesterolemic agent, comprising a hypocholesterolemic effective amount of [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid, its pharmaceutically acceptable salts or (2R-trans)-5-(4-fluorophenyl)-2-(1-methylethyl-N,4-diphenyl-1-[2-(tetrahydro-4-hydroxy-6-oxo-2H-pyran-2-yl)ethyl]-1H-pyrrole-3-carboxamide acid; and a pharmaceutically acceptable carrier. Further, the present invention is also a method of treating mammals, including humans, suffering from hypercholesterolemia by administering to such mammal a dosage form of the pharmaceutical composition described above.

DETAILED DESCRIPTION OF THE INVENTION

The pharmaceutically acceptable salts of the invention are those generally derived by dissolving the free acid or the lactone; preferably the lactone, in aqueous or aqueous alcohol solvent or other suitable solvents with an appropriate base and isolating the salt by evaporating the solution or by reacting the free acid or lactone; preferably the lactone and base in an organic solvent in which the salt separates directly or can be obtained by concentration of the solution.

In practice, use of the salt form amounts to use of the acid or lactone form. Appropriate pharmaceutically acceptable salts within the scope of the invention are those derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine and the like. Preferably, the lithium, calcium, magnesium, aluminum and ferrous or ferric salts are prepared from the sodium or potassium salt by adding the appropriate reagent to a solution of the sodium or potassium salt, i.e., addition of calcium chloride to a solution of the sodium or potassium salt of the compound of the formula I will give the calcium salt thereof.

The free acid can be prepared by hydrolysis of the lactone form of formula II or by passing the salt through a cationic exchange resin (H+resin) and evaporating the water.

The most preferred embodiment of the present invention is [R-(R*R*)]-2-(4-fluorophenyl)-β,δ-dihydroxy-5-(1-methylethyl)-3-phenyl-4-[(phenylamino)carbonyl]-1H-pyrrole-1-heptanoic acid, hemicalcium salt.

Generally, the compounds I and II of the present invention can be prepared by (1) resolving the racemate, that is prepared by the processes described in U.S. Pat. No. 4,681,893 which is incorporated by reference therefor, or (2) synthesizing the desired chiral form beginning from starting materials which are known or readily prepared using processes analogous to those which are known.

Specifically, resolution of the racemate may be accomplished as shown in Scheme I (where Ph is phenyl) as follows:

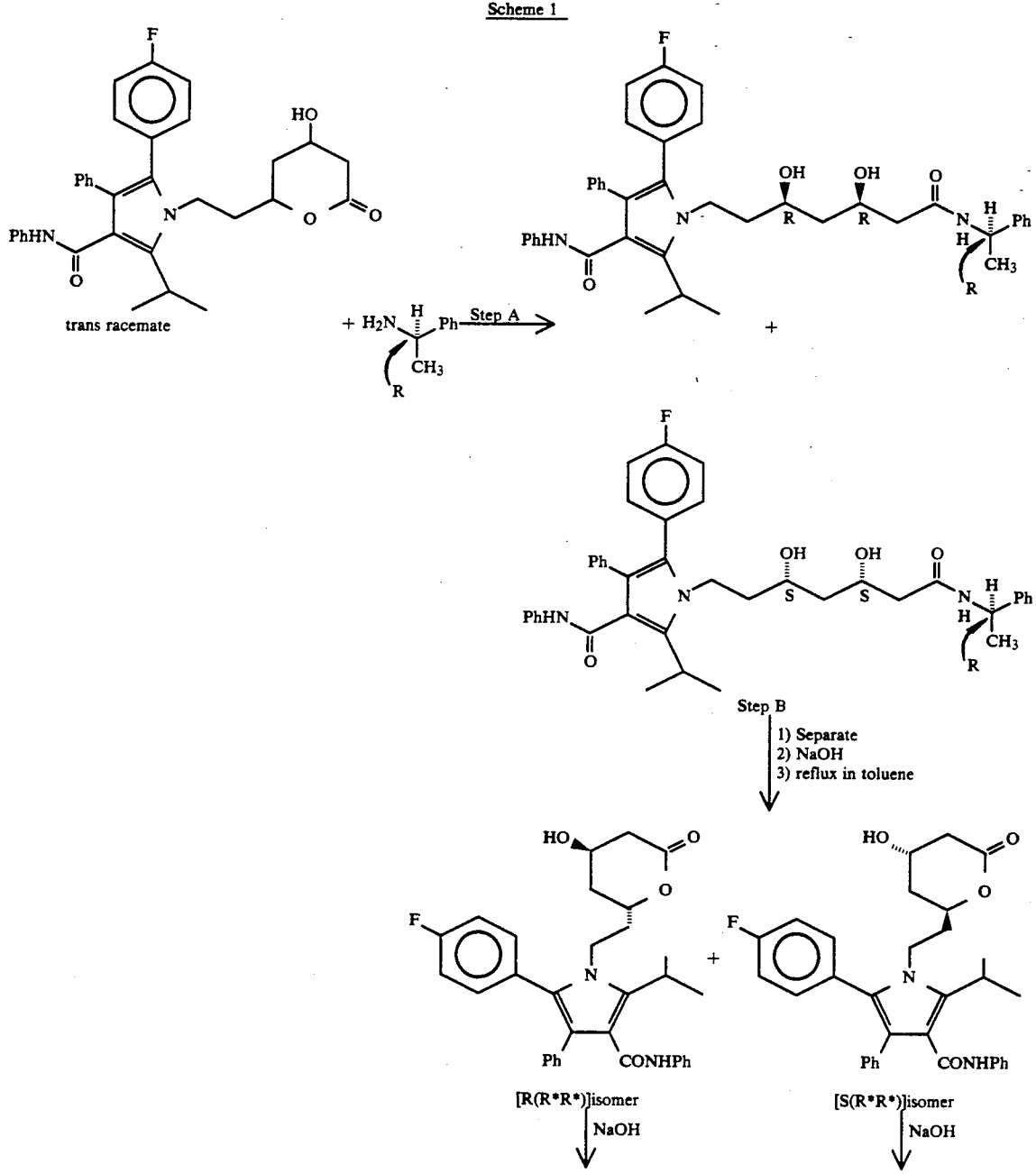

Scheme 1

-continued
Scheme 1
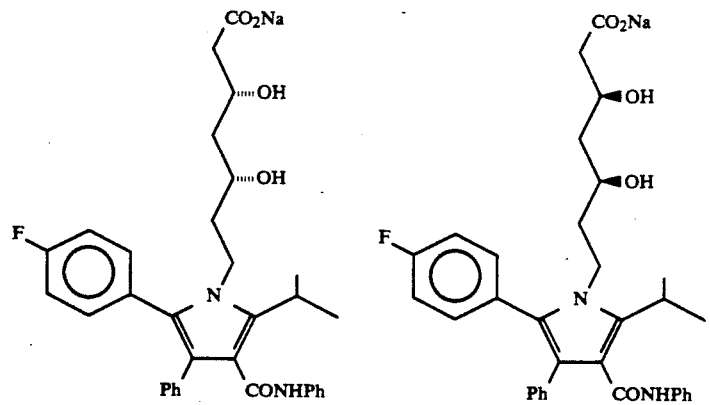
The "trans racemate" of Scheme 1 means a mixture of the following:
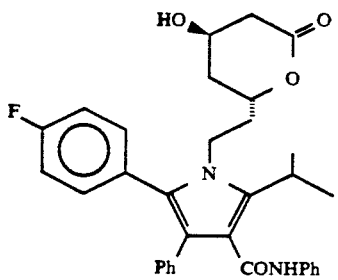
[R(R*R*)]isomer
and
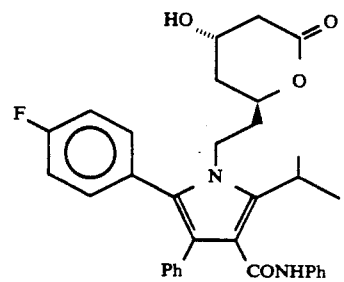
[S(R*R*)]isomer
The conditions of the Step 1 and 2 of Scheme 1 are generally as found in the Examples 6 and 7 hereinafter.
The chiral synthesis is shown in Scheme 2 (where Ph is phenyl) as follows:
Scheme 2
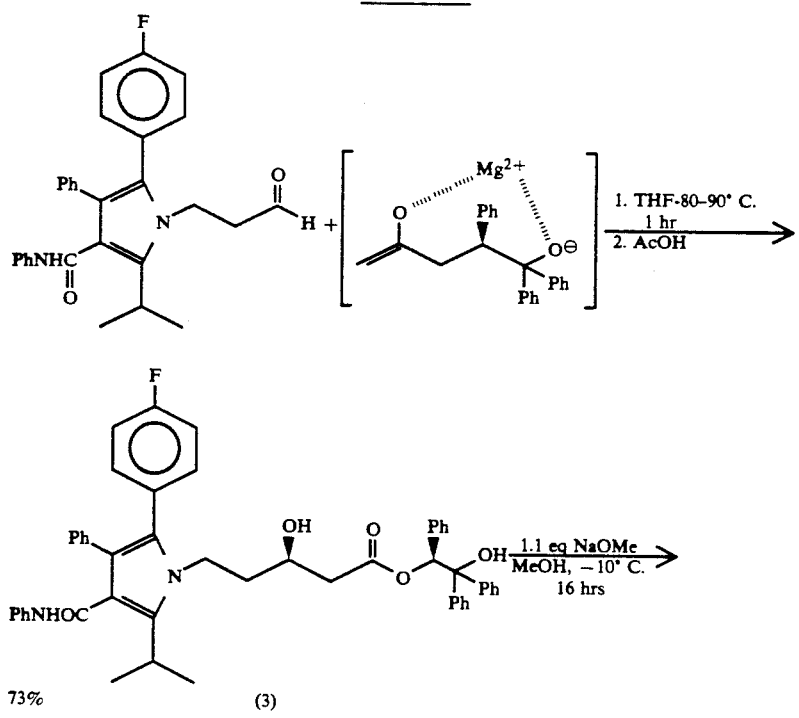

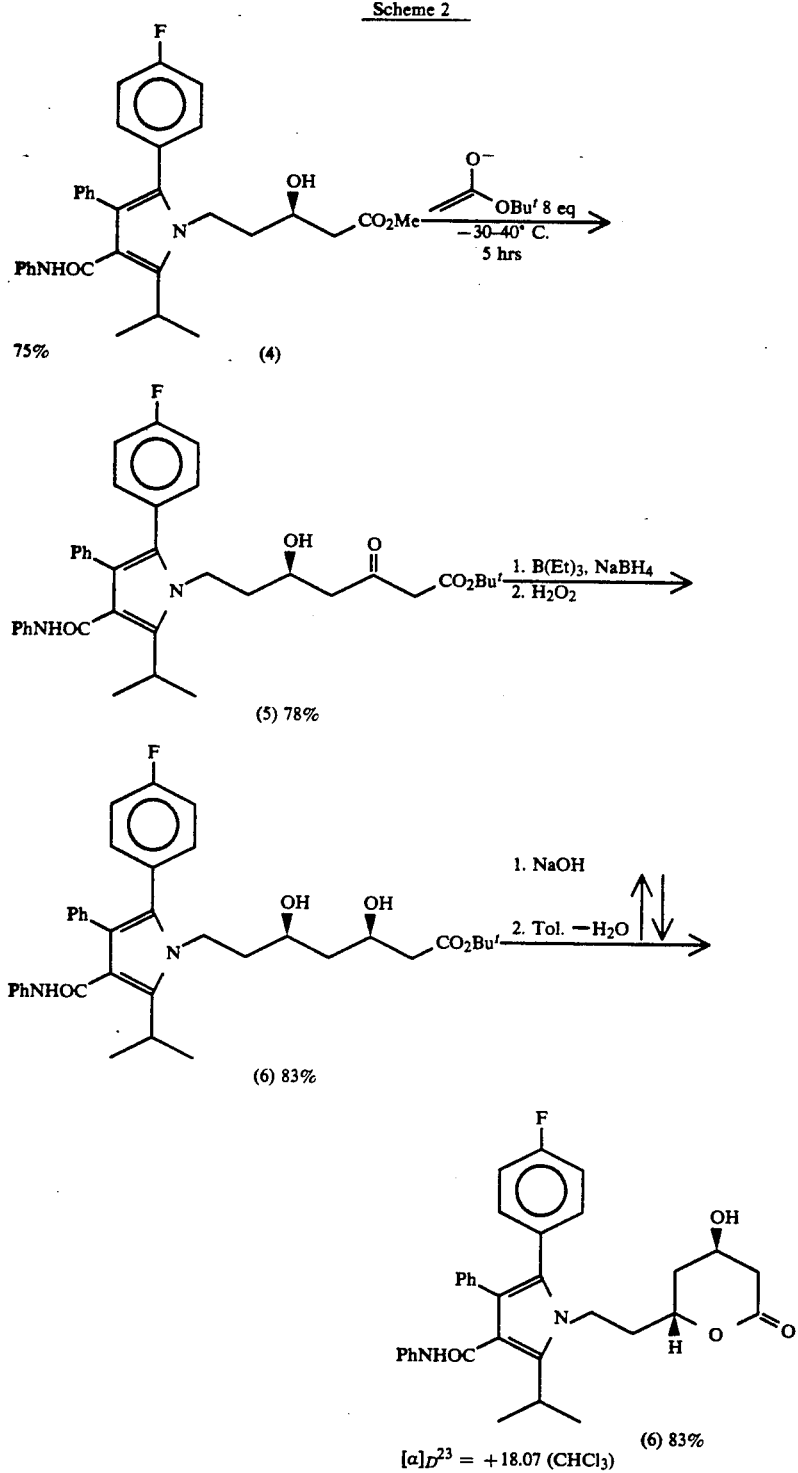

Generally, conditions for Scheme 2 are as shown in the Examples 1-5 hereinafter.

One of ordinary skill in the art would recognize variations in the Schemes 1 and 2 which are appropriate for the preparation of the compounds of the present invention.

The compounds according to present invention and especially according to the compound of the formula I inhibit the biosynthesis of cholesterol as found in the CSI screen that is disclosed in U.S. Pat. No. 4,681,893 which is now also incorporated by reference therefor. The CSI data of the compound I, its enantiomer the compound II and the racemate of these two compounds are as follows:

| Compound | $IC_{50}$ (micromoles/liter) |
| --- | --- |
| [R-(R*R*)] isomer | 0.0044 |

| Compound | IC$_{50}$ (micromoles/liter) |
| --- | --- |
| [S-(R*R*)] isomer | 0.44 |
| Racemate | 0.045 |

Accordingly, the present invention is the pharmaceutical composition prepared from the compound of the formula I or II or pharmaceutically acceptable salts thereof.

These compositions are prepared as described in U.S. Pat. No. 4,681,893 which is, therefore, again incorporated by reference here.

Likewise, the present invention is a method of use as hypolipidemic or hypocholesterolemic agents. The compounds of the present invention utilized in the pharmaceutical method of this invention are administered to the patient at dosage levels of from 10 to 500 mg per day which for a normal human adult of approximately 70 kg is a dosage of from 0.14 to 7.1 mg/kg of body weight per day. The dosages may be preferably from 0.5 to 1.0 mg/kg per day.

The dosage is preferably administered as a unit dosage form. The unit dosage form for oral or parenteral use may be varied or adjusted from 10 to 500 mg, preferably from 20 to 100 mg according to the particular application and the potency of the active ingredient. The compositions can, if desired, also contain other active therapeutic agents. Determinations of optimum dosages for a particular situation is within the skill of the art.

The compounds of the formula I and II and their pharmaceutically acceptable salts are in general equivalent for the activity of the utility as described herein.

The following examples illustrate particular methods for preparing compounds in accordance with this invention. These examples are thus not to be read as limiting the scope of the invention.

EXAMPLE 1

285 ml 2.2M n-butyl lithium (in Hexane) is added dropwise to 92 ml diisopropylamine in 300 ml THF at 50°-60° C. in a 1000 ml 1 neck flask via dropping funnel and under nitrogen. The well stirred yellow solution is allowed to warm to about −20° C. Then it is cannulated into a suspension of 99 g S(+)-2-acetoxy-1,1,2-triphenylethanol in 500 ml absolute THF, kept in a 2L-3 neck flask at −70° C. When addition is complete, the reaction mixture is allowed to warm to −10° C. over a period of two hours. Meanwhile, a suspension of 0.63 mol MgBr$_2$ is prepared by dropping 564 ml (0.63 mol) of bromine into a suspension of 15.3 g of magnesium (0.63 mol) in 500 ml THF plus in 3 L flask equipped with reflux condenser, and overhead stirrer. When this is completed, the MgBr$_2$ suspension is cooled to −78° C. and the enolate solution (dark brown) is cannulated into the suspension within 30 minutes. Stirring is continued for 60 minutes at −78° C. 150 g 5-(4-fluorophenyl)-2-(1-methylethyl)-1-(3-oxopropyl)-N,4-diphenyl-1H-pyrrole-3-carboxamide in 800 ml THF absolute was added dropwise over 30 minutes; then stirred for 90 minutes at −78° C., then quenched with 200 ml AcOH at −78° C. This is removed to a cool bath, 500 ml of H$_2$O is added and the mixture concentrated in vacuo at 40°-50° C. 500 ml of 1:1 EtOAc/Heptane is added to the yellowish slurry and filtered. The filtrate is washed extensively with 0.5N HCl, then several times with H$_2$O and finally with EtOAc/Heptane (3:1) that was cooled with dry ice to −20° C. The light brown crystalline product (Example 1A) is dried in vacuum oven at 40° C. The yield is 194 g.

The product 1A is recrystallized from EtOAc at −10° C. to yield 100 g to yield product 1B and then recrystallized from acetone/pentane to yield 90 g to yield product 1C. The mother liquor is combined from the wash of the crude material and recrystallized from EtOAc/Hexane. 33 g of 1B shows the following: HPLC: 97.4:2.17 of the R,S to S,S isomers. 28.5 g of 1C shows the following: HPLC:95.7:3.7. The combined 1B and 1C is recrystallized from CHCl$_3$ MeOH 10:1; providing a product 1F having a yield of 48.7 g of white crystal.

The mother liquor of the first aqueous wash is crystallized (EtOAc/Heptane) to yield product 1D of 21.4 g; HPLC: 71.56:25.52.

The mother liquor of 1B and 1C is combined and recrystallized from CHCl$_3$/MeOH/Heptane to yield 55.7 g white crystals of product 1G.

1D is recrystallized from CHCl$_3$/MeOH to yield the product 1H.

All mother liquor is combined, concentrated then the residue is dissolved in hot CHCl$_3$/MeOH 10:1; put on a silica gel column; and eluted with EtOAc/Hexane 40:60. The material crystallized out on the column and the silica gel is extracted with CHCl$_3$/MeOH and concentrated. Recrystallization of the residue from CHCl$_3$/Heptane 3:1 yields 33.7 g of product 1I.

The mother liquor of 1I is recrystallized to yield 18.7 g of product 1K.

The mother liquor of 1K is crystallized to yield 6.3 g of product 1L.

1I, 1K and 1L is combined and recrystallized from CHCl$_3$/Heptane to yield 48 g.

The combined mother liquor of 1I, 1K, and 1L is concentrated to yield 31 g of 1M.

The product 1F provides the following data.

| Anal: 1F m.p. 229-230° C. | |
| --- | --- |
| Calc. | Found |
| C: 77.84 | 77.14 |
| H: 6.02 | 6.45 |
| N: 3.56 | 3.13 |

These data are consistent with the formula

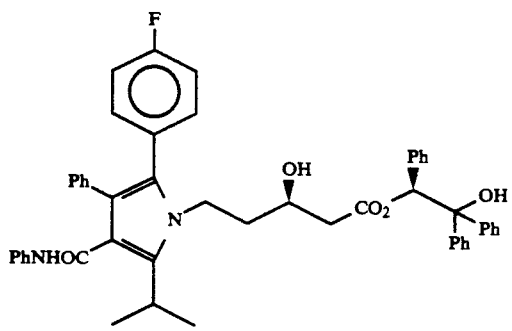

EXAMPLE 2

162 g (0.206M) of the combined products 1F, 1G, 1H and 1L of Example 1 are suspended in 800 ml Methanol/THF (5:3). Cooled to 0° C. and added to 11.7 g sodium methoxide. The mixture is stirred until everything is dissolved, then put in the freezer overnight. The reaction mixture is allowed to warm to room temperature, quenched with 15 ml HOAc, then concentrated in vacuo at 40° C. to obtain expected product as follows:

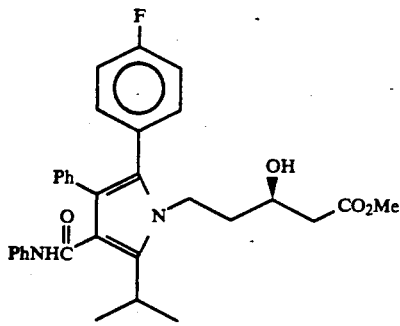

This product is added to 500 ml H₂O and extracted twice with EtOAc (300 ml). The combined extracts are washed with saturated NaHCO₃, brine, dried over anhydrous magnesium sulfate, filtered and the solvent evaporated. The residue is chromatographed on silica gel in EtOAc/Heptane (1:4) as eluent to yield 109 g colorless oil which is recrystallized from Et₂O/Heptane to yield:

73.9 g first crop; white crystals
8.2 g second crop; white crystals.
The crystals provide the following data:
m.p. 125°-126° C., $a_D^{20}$=4.23° (1.17M, CH₃OH)

| Calc. | Found |
| --- | --- |
| C: 72.76 | 72.51 |
| H: 6.30 | 6.23 |
| N: 5.30 | 5.06 |

These data are consistent with the formula

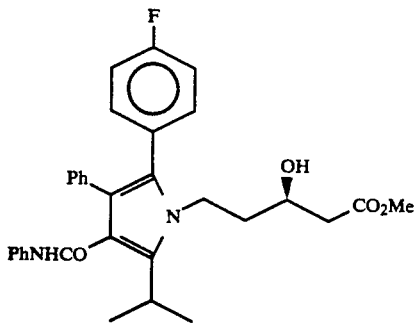

EXAMPLE 3

77 ml of diisopropylamine is dissolved in 250 ml THF in a 2000 ml three-neck flask equipped with thermometer and dropping funnel. The reaction mixture is kept under nitrogen. The mixture is cooled to −42° C. and added to 200 ml 2.2M of n-butyl lithium (in Hexane) dropwise over 20 minutes and stirred for 20 minutes before adding dropwise 62 ml of t-butylacetate, dissolved in 200 ml THF (over about 30 minutes). This mixture is stirred 30 minutes at −40° C., then 140 ml 2.2M of n-butyl lithium is added over 20 minutes. When addition is complete, 81 g of the product of Example 2 in 500 ml absolute THF is added as quickly as possible without allowing the temperature to rise above −40° C.

Stirring is continued for four hours at −70° C. The reaction mixture is then quenched with 69 ml glacial acetic acid and allowed to warm to room temperature. The mixture is concentrated in vacuo and the residue is taken up in EtOAc, washed with water extensively, then saturated NH₄Cl, NaHCO₃ (saturated), and finally with brine. The organic layer is dried over anhydrous MgSO₄, filtered and the solvent evaporated. The NMR of the reaction is consistent with starting material plus product in about equal amounts plus some material on the baseline of the TLC. The material of the baseline of the TLC is separated from starting material and the product is extracted by acid/base extraction. The organic phase is dried and concentrated in vacuo to yield 73 g. The NMR and TLC are consistent with the formula

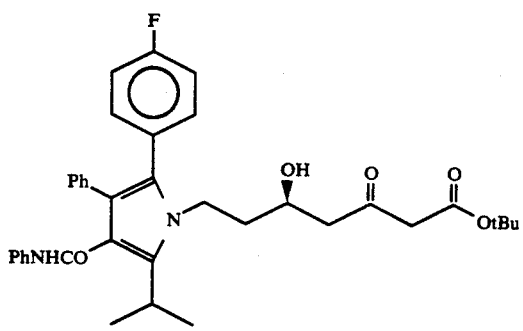

EXAMPLE 4

73 g crude product of Example 3 is dissolved in 500 ml absolute THF and 120 ml triethyl borane is added, followed by 0.7 g t-butylcarboxylic acid. The mixture is stirred under a dry atmosphere for 10 minutes, cooled to −78° C. and 70 ml methanol is added and followed by 4.5 g sodium borohydride. The mixture is again stirred at −78° C. for six hours. Then poured slowly into a 4:1:1 mixture of ice/30% H₂O₂/H₂O. This mixture is stirred overnight then allowed to warm to room temperature.

CHCl₃ (400 ml) is added and the mixture is partitioned. The water layer is extracted again with CHCl₃. The organic extracts are combined and washed extensively with H₂O until no peroxide could be found. The organic layer is dried over MgSO₄, filtered and the solvent is evaporated.

The residue is treated by flash chromatography on silica gel, i.e. EtOAc/Hexane 1:3 to yield 51 g.

The product is dissolved in THF/MeOH and added to 100 ml in NaOH, then stirred for four hours at room temperature. The solution is concentrated at room temperature to remove organic solvent, added to 100 ml H₂O, and extracted with Et₂O twice. The aqueous layer is acidified with 1N HCl and extracted with EtOAc three times. The combined organic layers are washed with H₂O. The organic layer is dried with anhydrous MgSO₄, filtered, and the solvent evaporated. The residue is taken up in 2 liters of toluene and heated to reflux using a Dean-Stark trap for 10 minutes.

The reaction mixture is allowed to cool to room temperature overnight. Reflux is repeated for 10 minutes and cooled for 24 hours.

The procedure above is repeated. The reaction is left at room temperature for the next 10 days, then concentrated to yield 51 g of colorless foam.

This product is dissolved in minimum $CHCl_3$ and chromatographed on silica gel eluting with EtOAc/Heptane (50:50) to yield 23 g in pure material.

Chromatography on silica gel in $CHCl_3$/2-propanol (98.5:1.5) yields 13.2 g.

| Calc. |
| --- |
| C: 73.31 |
| H: 6.15 |
| N: 5.18 |

EXAMPLE 5

Preparation of 2R-trans-5-(4-fluorophenyl)-2-(1-methylethyl)-N,4-diphenyl-1-[2-tetrahydro-4-hydroxy-6-oxo-2H-pyran-2-yl)ethyl]-1H/-pyrrole-3-carboxamide The product of Example 4 is recrystallized from EtOAc/Hexane. Fraction 1 yields 8.20 g of 4A. The mother liquor yields 4.60 g of 4B, HPLC of 4B shows 100% of the product to be the [R-(R*R*)] isomer. 4A is recrystallized to yield 4.81 g of 4C. 4B is chromatographed on silica gel in $CHCl_3$/2-propanol to yield 4.18 g colorless foam of 4D showing $a_D^{23}+24.53°$ (0.53% in $CHCl_3$). 4C is recrystallized and the mother liquor of 4C is to yield 2.0 g.HPLC which indicates 100% of the R-trans isomer 2R-trans-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamide.

EXAMPLE 6

Preparation of diastereomeric α-methylbenzylamides

A solution of the racemate, trans-(±)-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamide, (30 g, 55.5 ml) in (R)-(+)-α-methylbenzylamine (575 ml, 4.45 mol, 98% Aldrich) is stirred overnight at room temperature.

The resulting solution is then diluted with ether (2 l) and then washed exhaustively with 2M HCl (4×500 ml), water (2×500 ml) and brine (2×500 ml). The organic extract is then dried over $MgSO_4$, filtered and concentrated in vacuo to yield 28.2 g of the diastereomeric α-methylbenzylamides as a white solid; m.p. 174.0°-177°. The α-methylbenzylamides are separated by dissolving 1.5 g of the mixture in 1.5 ml of 98:1.9:0.1 $CHCl_3$:$CH_3OH$:$NH_4OH$ (1000 mg/ml) and injecting onto a preparative HPLC column (silica gel, 300 mm×41.4 mm I.D.) by gastight syringe and eluting with the above solvent mixture. Fractions are collected by UV monitor. Diastereomer 1 elutes at 41 minutes. Diastereomer 2 elutes at 49 minutes. Center cut fractions are collected. This procedure is repeated three times and the like fractions are combined and concentrated. Examination of each by analytical HPLC indicates that diastereomer 1 is 99.84% pure and diastereomer 2 is 96.53% pure. Each isomer is taken on separately to following Examples.

EXAMPLE 7

Preparation of 2R-trans-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide To an ethanolic solution (50M) of diastereomer 1 of Example 6, [3R-[3R*(R*),5R*]]-2-(4-fluorophenyl)-[β],[δ]-dihydroxy-5-(1-methylethyl)-3-phenyl-4-[(phenylamino) carbonyl]-N-(1-phenylethyl-1H-pyrrole-1-heptanamide, (hydroxy centers are both R) (1 g, 1.5 mmol) is added 1N NaOH (3.0 ml, 3 mmol). The resulting solution is heated to reflux for 48 hours.

The solution is cooled to room temperature and concentrated in vacuo. The residue is resuspended in water and carefully acidified with 6N HCl. The resulting acidic solution is extracted with ethyl acetate. The organic extract is washed with water, brine, dried over $MgSO_4$, filtered and concentrated in vacuo. This residue is redissolved in toluene (100 ml) and heated to reflux with azeotropic removal of water for three hours. This is cooled to room temperature and concentrated in vacuo to yield 1.2 g of a yellow semi-solid. Flash chromatography on silica gel eluting with 40% EtOAc/Hexane gives 0.42 g of a white solid which still contains impurities. This is rechromatographed to give 0.1 g of essentially pure R,R, enantiomer, 2R-trans-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide, as a white foam. HPLC shows this material to be 94.6% chemically pure $[\alpha]_D^{23}$:0.51% in $CHCl_3$=25.5°. The peak at room temperature=53.46 minutes is tentatively assigned to an unknown diastereomer resulting from the 2% (S)-(−)-α-methylbenzylamine present in the Aldrich α-methylbenzylamine.

EXAMPLE 8

Preparation of 2S-trans-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide-(S,S enantiomer of the compound prepared in Example 5

Carrying out the procedure described in Example 7 on diastereomer 2 afforded 0.6 g of a foamy solid which was flash chromatographed on silica gel. Elution with 50% EtOAc/Hexane gave 0.46 g of essentially pure S,S, enantiomer 2S-trans-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide, as a white foam. HPLC showed this material to be 97.83% chemically pure. $[\alpha]_D^{23}=0.51\%$ in $CHCl_3=-24.8\%$.

EXAMPLE 9

Hydrolysis of chemical lactone of formula II

To a room temperature, solution of the lactone in THF is added a solution of sodium hydroxide in water. The mixture is stirred for two hours HPLC:99.6% (product); 0.34 to (starting lactone). The mixture is diluted with 3 L water, extracted with ethyl acetate (2×1 L) and acidified to pH×4 by addition of 37 ml of 5N hydrochloric acid. The aqueous layer is extracted with 2×1.5 L portions of ethyl acetate. The combined ethyl acetate extracts are washed with 2×1 L of water, brine and dried, gave after filtration the ethyl acetate solution of the required face-acid. This solution is used directly in the fraction of the N-methylglucamine salt.

The ethyl acetate extracts from the brine-water were concentrated to give 15.5 g of an off-white solid.

EXAMPLE 10

Calcium Salt from Sodium Salt and/or Lactone

Dissolve one mole lactone (540.6 g) in 5 L of MeOH; after dissolution add 1 L $H_2O$. While stirring, add one equivalent NaOH and follow by HPLC until 2% or less lactone and methyl ester of the diolacid remains (cannot use an excess of NaOH, because Ca(OH)$_2$ will form an addition of CaCl$_2$). Charge NaOH as caustic (51.3 ml, 98 eq.) or as pellets (39.1 g, 0.98 eq.).

The above procedure is shown as follows:

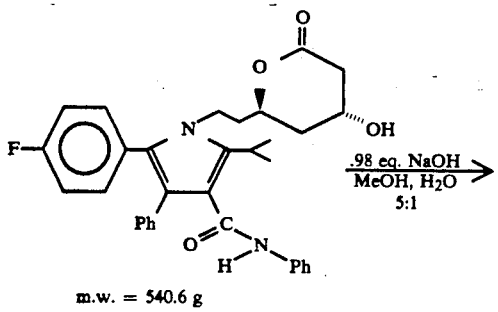

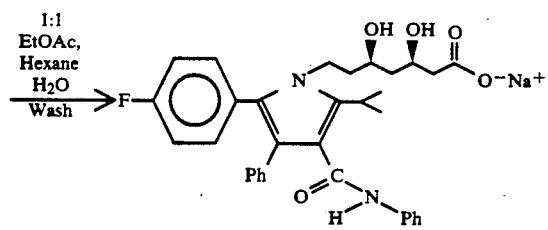

Upon completion of hydrolysis, add 10 L H$_2$O, then wash at least two times with a 1:1 mixture of EtOAc/-Hexane. Each wash should contain 10 L each of EtOAc/Hexane. If sodium salt is pure, add 15 L of MeOH. If it is impure and/or contains color, add 100 g of G-60 charcoal, stir for two hours and filter over supercel. Wash with 15 L MeOH. Perform a wt/vol % on the reaction mixture, by HPLC, to determine the exact amount of salt in solution.

Dissolve 1 eq. or slight excess CaCl$_2$.2H$_2$O (73.5 g) in 20 L H$_2$O. Heat both reaction mixture and CaCl$_2$ solution to 60° C. Add CaCl$_2$ solution slowly, with high agitation. After complete addition, cool slowly to 15° C. and filter. Wash filter cake with 5 L H$_2$O. Dry at 50° C. in vacuum oven.

Can be recrystallized by dissolving in 4 L of EtOAc (50° C.) filtering over supercel, washing with 1 L EtOAc, then charging 3 L of hexane to the 50° C. rxn solution.

The above procedure is shown as follows:

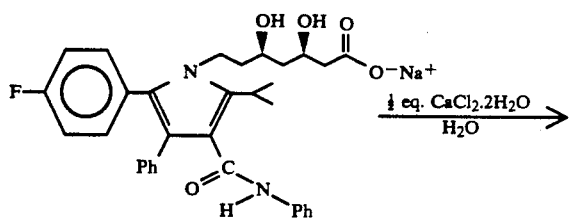

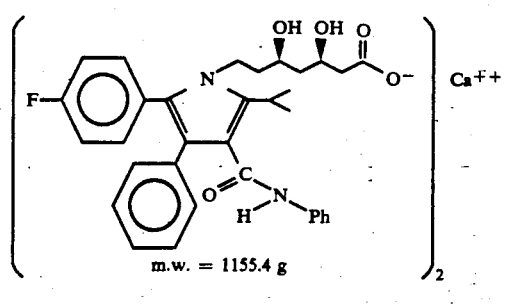

EXAMPLE 11

Treatment of Ethyl Acetate Solution of Free-acid of the Formula I with N-methylglucamine To a solution of the free-acid of the formula I (0.106M) in ethyl acetate (3 L) is added a solution of N-methylglucamine (20.3 g, 0.106 m) in (1:1) water-acetone (120 ml, 120 ml) with vigorous stirring at room temperature. Stirring is continued for 16 hours and the hazy solution concentrated in vacuo to ~250 mp. Toluene (1 L) is added and the mixture concentrated to a white solid ~100 g. The solid is dissolved in 1670 ml acetone and filtered into a three-neck flask equipped with a mechanical stirrer and thermostat controlled thermometer. The flask and filter is washed with 115 ml (1:1) water-acetone and the clear solution is cooled slowly. This provided a precipitate which is re-dissolved by heating back to 65° C. Addition of a further 20 ml of water followed by the washing gives a crystalline product which was isolated by filtration. The solids are washed with 1200 ml CH$_3$Cl and vacuum dried at 255° to give a white solid. Analysis of this material indicates that it contains 4% amine as well as 0.4% residual acetone and 0.67% water. Analytical results are noted as follows:

Melting point: 105°–155° C. (decomposition) Analysis Expected: C=63.73; H-6.95; N=5.57; F2=9.53. Analysis Found: C=62.10; H-6.89; N-5.34; F2. C=61.92; H-7.02; N=5.38; F2.

H$_2$O=0.47% (KF)

HPLC: MeOH, H$_2$O, THF (40; 550; 250)
 Econosil: C18, 5 $\mu$, 25 CM
 256 nm: 1.0 ml/min.
 6–81 min.: 98.76%

Opt. Ret.: [$\alpha$]·b= −10.33° (c=1.00, MeOH)

Residual Solvents: CH$_2$CH=0.26%

Titrations:
 HClO$_4$ (0.1N)=203.8%
 Bu$_4$NOH (0.1N)=98.5%

Other salts prepared in a manner analogous to those processes appropriately selected from Examples 10 and 11 above may be the potassium salt, hemimagnesium salt, hemizinc salt or the 1-deoxy-2-(methylamino)-D-glucitol complex of the compound of formula I.

I claim:

1. [R-(R*,R*)]-2-(4-fluorophenyl)-$\beta$,$\delta$-dihydroxy-5-(1-methylethyl)-3-phenyl-4-[(phenylamino)-carbonyl]-1H-pyrrole-1-heptanoic acid or (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide; or pharmaceutically acceptable salts thereof.

2. A compound of claim 1 which is [R-(R*R*)]-2-(4-fluorophenyl)-$\beta$-$\delta$-dihydroxy-5-(1-methylethyl)-3-phenyl-4-[(phenylamino)carbonyl]-1H-pyrrole-1-heptanoic acid.

3. A compound of claim 1 which is (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

4. The monosodium salt of the compound of claim 2.

5. The monopotassium salt of the compound of claim 2.

6. The hemicalcium salt of the compound of claim 2.

7. The N-methylglucamine salt of the compound of claim 2.

8. The hemimagnesium salt of the compound of claim 2.

9. The hemizinc salt of the compound of claim 2.

10. The 1-deoxy-1-(methylamino)-D-glucitol mixture with the compound of claim 2.

11. A pharmaceutical composition for treating hypercholesterolemia comprising a hypocholesterolemic effective amount of a compound of claim 1 and a pharmaceutically acceptable carrier.

12. A method of inhibiting cholesterol synthesis in a human suffering from hypercholesterolemia comprising administering a compound of claim 1 in unit dosage form.

* * * * *